United States Patent
Rao et al.

(10) Patent No.: US 9,622,885 B2
(45) Date of Patent: Apr. 18, 2017

(54) COLLAPSIBLE, SHAPE MEMORY ALLOY STRUCTURES AND FOLDING FIXTURES FOR COLLAPSING SAME

(71) Applicant: Medplate LifeSciences Corporation, Bridgeville, PA (US)

(72) Inventors: Rob K Rao, Moraga, CA (US); Richard Thomas Briganti, Philadelphia, PA (US); Michael D Black, Palo Alto, CA (US); Mike Y Chen, San Marino, CA (US)

(73) Assignee: MEDPLATE LIFESCIENCES CORPORATION, Bridgeville, PA (US)

( * ) Notice: Subject to any disclaimer, the term of this patent is extended or adjusted under 35 U.S.C. 154(b) by 157 days.

(21) Appl. No.: 14/550,636

(22) Filed: Nov. 21, 2014

(65) Prior Publication Data
US 2015/0148886 A1 May 28, 2015

Related U.S. Application Data

(63) Continuation of application No. PCT/US2013/041943, filed on May 21, 2013.
(Continued)

(51) Int. Cl.
*A61F 2/82* (2013.01)
*A61L 27/04* (2006.01)
(Continued)

(52) U.S. Cl.
CPC ............. *A61F 2/82* (2013.01); *A61F 2/07* (2013.01); *A61F 2/2412* (2013.01); *A61F 2/2418* (2013.01); *A61L 27/04* (2013.01); *B23K 35/0222* (2013.01); *B23K 35/0255* (2013.01); *B23K 35/32* (2013.01); *B32B 1/08* (2013.01); *B32B 7/045* (2013.01); *B32B 15/01* (2013.01); *C22C 19/03* (2013.01); *C22C 19/058* (2013.01); *C22C 27/02* (2013.01);
(Continued)

(58) Field of Classification Search
CPC .................................... A61F 2/06; A61F 2/82
USPC .................................................. 623/1.1–1.48
See application file for complete search history.

(56) References Cited

U.S. PATENT DOCUMENTS 5,037,427 A 8/1991 Harada et al.
5,197,978 A 3/1993 Hess
(Continued)

FOREIGN PATENT DOCUMENTS

SU 1251886 8/1986
WO 02/41929 5/2002
(Continued)

*Primary Examiner* — Suzette J Gherbi
(74) *Attorney, Agent, or Firm* — Blynn L. Shideler; Krisanne Shideler; BLK Law Group

(57) ABSTRACT

A shape memory alloy structure comprises at least one tubular member formed of shape memory material, each tubular member including a plurality of panels having side edges, wherein each tubular member is moveable between a radially contracted position and a radially extended position, and wherein the coupled side edges of adjacent panels of each tubular member form hinges for moving the structure between the contracted position and the extended position. Multiple layer tubular structures, methods for forming and fixtures for collapsing same are also disclosed.

17 Claims, 9 Drawing Sheets

US 9,622,885 B2
Page 2

Related U.S. Application Data

(60) Provisional application No. 61/649,431, filed on May 21, 2012.

(51) Int. Cl.

| | | |
|---|---|---|
| *A61F 2/07* | (2013.01) | |
| *B32B 1/08* | (2006.01) | |
| *A61F 2/24* | (2006.01) | |
| *B32B 7/04* | (2006.01) | |
| *B32B 15/01* | (2006.01) | |
| *C22C 19/03* | (2006.01) | |
| *C22C 19/05* | (2006.01) | |
| *C22C 27/02* | (2006.01) | |
| *B23K 35/32* | (2006.01) | |
| *B23K 35/02* | (2006.01) | |

(52) U.S. Cl.
CPC ........... *A61F 2210/0014* (2013.01); *A61F 2230/0069* (2013.01); *A61L 2400/16* (2013.01); *B32B 2307/718* (2013.01)

(56) References Cited

U.S. PATENT DOCUMENTS

| | | | |
|---|---|---|---|
| 5,716,410 A | 2/1998 | Wang et al. | |
| 5,964,744 A | 10/1999 | Balbierz et al. | |
| 6,245,103 B1 | 6/2001 | Stinson | |
| 6,348,067 B1 | 2/2002 | Baum et al. | |
| 6,413,273 B1 | 7/2002 | Baum et al. | |
| 6,475,234 B1 | 11/2002 | Richter et al. | |
| 7,896,222 B2 | 3/2011 | Shaw et al. | |
| 8,273,194 B2 | 9/2012 | Shaw et al. | |
| 8,465,847 B2 | 6/2013 | Shaw et al. | |
| 2001/0034550 A1 | 10/2001 | Buirge et al. | |
| 2007/0027473 A1 | 2/2007 | Vresh et al. | |
| 2007/0203560 A1* | 8/2007 | Forster | A61F 2/2418 623/1.11 |
| 2009/0149941 A1 | 6/2009 | Hasson et al. | |
| 2011/0054588 A1* | 3/2011 | Xu | A61L 27/3604 623/1.13 |
| 2012/0016422 A1* | 1/2012 | Hua | A61B 17/7083 606/264 |
| 2012/0109183 A1* | 5/2012 | Belson | A61F 2/01 606/200 |
| 2014/0343664 A1* | 11/2014 | Furey | A61F 2/06 623/1.18 |
| 2015/0051694 A1* | 2/2015 | Furey | A61F 2/82 623/1.15 |

FOREIGN PATENT DOCUMENTS

| | | |
|---|---|---|
| WO | 03/099165 | 4/2003 |
| WO | 2004/010901 | 5/2004 |
| WO | 2004092581 | 10/2004 |
| WO | 2005/044330 | 5/2005 |
| WO | 2007136866 | 11/2007 |
| WO | 2013/177109 | 11/2013 |

* cited by examiner

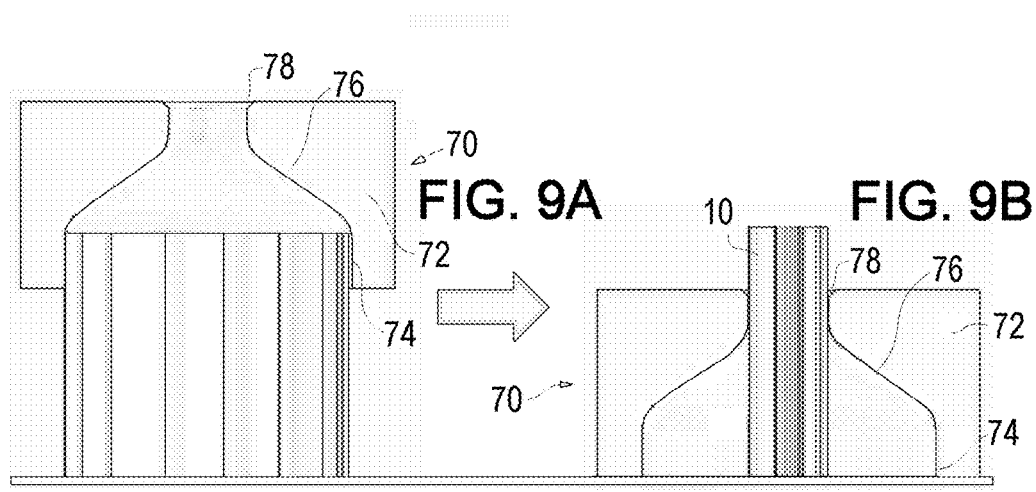
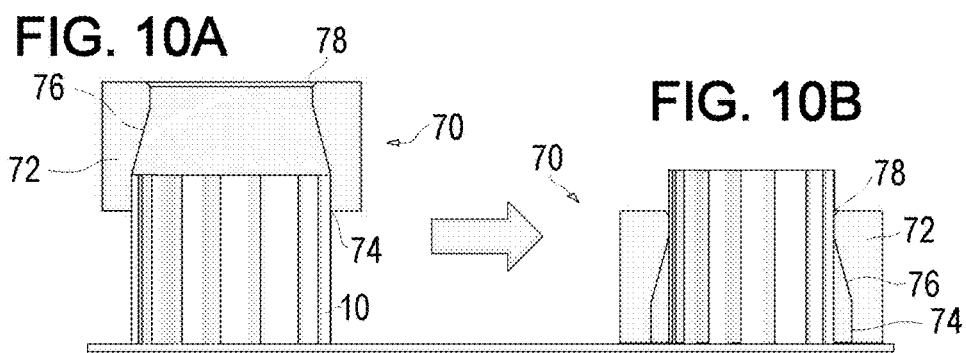
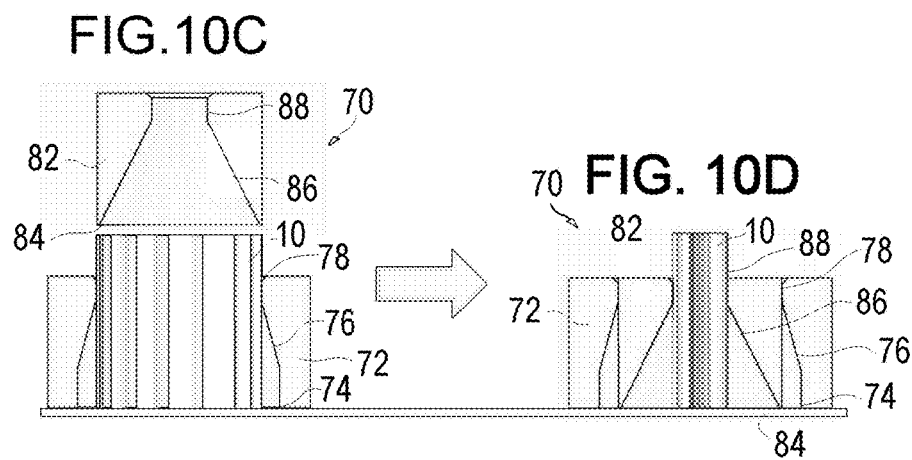

COLLAPSIBLE, SHAPE MEMORY ALLOY STRUCTURES AND FOLDING FIXTURES FOR COLLAPSING SAME

RELATED APPLICATIONS

This application is a continuation of international patent application serial number PCT/US2013/041943 filed May 21, 2014 and which designated the United States and is entitled "Collapsible, Shape Memory Alloy Structures and Folding Fixtures for Collapsing Same." International patent application serial number PCT/US2013/041943 claims priority to U.S. provisional patent application Ser. No. 61/649,431 filed May 21, 2012, entitled "Collapsible, Shape Memory Alloy Structures and Method for Forming Same" which prior applications are incorporated herein by reference in its entirety.

BACKGROUND OF THE INVENTION

1. Field of the Invention

The present invention relates to collapsible shape memory alloy structures, and more particularly to lightweight or low profile, collapsible, shape memory alloy structures and method for forming same. Such collapsible, shape memory alloy structures may be formed as cardiovascular stents, cardiovascular valves, filters, closure devices, drug delivery devices, pumps or stents for any lumen or tissue in or outside of the body, or even an electronic component.

2. Background Information

Materials combining ultra-low density with the desirable characteristics of metals have been under technical development for decades, and a variety of metals and alloys are commercially available in various cellular forms. Cellular structures made from shape-memory alloys (SMAs), most commonly nitinol, are particularly intriguing for their potential to deliver shape memory and/or superelasticity in a lightweight material. Shape memory refers to the ability of SMA to undergo deformation at one temperature, then recover its original, un-deformed shape upon heating above its "transformation temperature." Superelasticity occurs at a narrow temperature range just above its transformation temperature; in this case, no heating is necessary to cause the undeformed shape to recover, and the material exhibits enormous elasticity, some 10-30 times that of ordinary metal.

Over 20 years ago a survey focused on predicting the then future technology, market, and applications of SMA's. The companies predicted the following uses of nitinol in a decreasing order of importance: (1) Couplings, (2) Biomedical and medical, (3) Toys, demonstration, novelty items, (4) Actuators, (5) Heat Engines, (6) Sensors, (7) Cryogenically activated die and bubble memory sockets, and finally (8) lifting devices. Many of these applications have come to pass. One significant application of nitinol in medicine is in stents because a collapsed stent can be inserted into a vein and return to its original expanded shape helping to improve blood flow. The biocompatibility of nitinol has made it essentially a material of choice in biomedical device developments. Nitinol is known in a variety of other common applications such as extremely resilient glasses frames, some mechanical watch springs, retractable cell phone antennas, microphone booms, due to its highly flexible & mechanical memory nature.

Some methods of forming SMA structures are described in U.S. Pat. No. 7,896,222 which is incorporated herein by reference and relates to a transient-liquid reactive brazing method that allows the fabrication of low density metal alloy structures, such as cellular or honeycomb structures, wire/tube space-frames, or other sparse built-up structures using nitinol (near-equiatomic titanium-nickel alloy) or related shape-memory and superelastic alloys, or high temperature SMAs, such as NiTi X alloys, wherein X is Hf or Zr substituted for Ti and/or X is Cu, Pd, Pt and/or Au substituted for Ni, e.g., NiTiCu or TiNiPd. More particularly, shape memory alloys (SMAs), in forms such as corrugated sheets, discrete tubes, wires, or other SMA shapes are joined together using a transient-liquid reactive metal joining technique, wherein a brazing metal contacts an SMA, like nitinol, at an elevated temperature. The brazing metal, preferably niobium, liquefies at a temperature below the melting point of both the brazing metal and the SMA, and readily flows into capillary spaces between the elements to be joined, thus forming a strong joint. In this method, no flux is required and the joined structures are biocompatible. See also U.S. Pat. Nos. 8,273,194 and 8,465,847 which are incorporated herein by reference and which disclose methods of manufacture of shape-memory alloy cellular materials and structures by transient-liquid reactive joining.

U.S. Publication 2009-0149941, which is incorporated herein by reference, is directed to a compressed tubular tissue support structure that can easily be introduced into vessels requiring support. This reference notes that in medical fields the "Introduction of a stent into a hollow organ is difficult When the stent is introduced into the hollow organ there is a risk that the surrounding tissue will be injured by abrasion in the process, because the stent is too large and has sharp edges. The shape-memory effect is therefore also used again to reduce the diameter of the stent when the stent is in turn to be removed. Examples of removable stents composed of metals with shape-memory properties are known, for example, in: U.S. Pat. Nos. 6,413,273; 6,348,067; 5,037,427; and 5,197,978"; and these patents are incorporated herein by reference. U.S. Pat. Nos. 5,716,410, 5,964,744, 6,245,103 and 6,475,234 and WIPO documents WO 2002/041929, WO 2003/099165, WO 2004/010901, and WO 2005/044330 are also discussed as relevant disclosure of SMA stent designs and these patents and documents are incorporated herein by reference.

There remains a need to expand the available lightweight, collapsible, shape memory alloy structures for applications in numerous fields.

SUMMARY OF THE INVENTION

One aspect of the present invention provides a shape memory alloy structure that may include at least two layers formed of shape memory material. Each layer is formed with a plurality of panels having side edges, wherein at least some of the adjacent layers are coupled together at selected edges of adjacent panels. The structure is moveable between a contracted position and an extended position and wherein the coupled edges may form hinges for moving the structure between the contracted position and the extended position. The edges of the panels are referenced as hinges in that, as described below, the panels move to a contracted position effectively relative to edges that comprise the relatively unbendable part of the structure, similar to a hinge pin. In the present design, as described below these edges are essentially the stiff joints and the "bearing" surfaces for crimping and later outer diameter support of whatever may encloses it the structure.

The invention provides a shape memory alloy structure including at least one tubular member formed of shape memory material. Each tubular member includes a plurality of panels having side edges, wherein each tubular member is moveable between a radially contracted position and a radially extended position. The coupled side edges of adjacent panels of each tubular member form hinges for moving the structure between the contracted position and the extended position.

The invention also provides a shape memory alloy structure comprising at least one tubular member formed of shape memory alloy, each tubular member formed of a plurality of concave panels wherein circumferentially adjacent panels are coupled at substantial tangential portions of each circumferentially adjacent panels, and wherein each tubular member is formed for movement of the shape memory alloy structure between a contracted position and a radially extended position.

The invention also provides a shape memory alloy structure comprising at least two substantially concentric tubular members formed of shape memory alloy. Each tubular member is formed of a plurality of scalloped panels separated by peaks. At least some of the peaks of at least one concentrically inner of the tubular members are aligned with adjacent peaks of the immediately outwardly adjacent tubular member.

The invention provides a shape memory alloy structure including at least one tubular member formed of shape memory alloy and formed of a plurality of substantially solid scalloped panels separated by peaks. The structure is moveable between a radially contracted position and a radially extended position, wherein the effective outer diameter of the structure in the radially extended position is at least 3.5 times the effective outer diameter of the structure in the radially contracted position.

The invention provides a method of compacting a collapsible shape memory alloy structure comprising the steps of (a) providing a folding fixture with a body member having an inlet opening of a first diameter at one end thereof and a smaller diameter outlet at an opposite end thereof and a converging surface extending between the inlet opening and the outlet opening; and (b) passing the collapsible shape memory alloy structure entirely through the inlet opening and the outlet opening of the folding fixture.

The invention provides a method of manually compacting a collapsible shape memory alloy structure comprising the steps of (a) providing a folding fixture with a strap; (b) looping the strap about the perimeter of the collapsible shape memory alloy structure; manually tightening the strap about the perimeter of the collapsible shape memory alloy structure.

The invention provides a method of compacting a collapsible shape memory alloy structure, comprising the steps of (a) providing a shape memory alloy structure which includes at least one tubular member formed of shape memory alloy, each tubular member formed of a plurality of concave panels wherein circumferentially adjacent panels are coupled at hinges for movement of the shape memory alloy structure between a contracted position and a radially extended position; (b) providing a folding fixture having a plurality of radially moveable pins; (c) engaging the pins with the panels of the shape memory alloy structure; (d) moving the pins radially inwardly while in contact with the panels of the shape memory alloy structure to compact the shape memory alloy structure.

The invention provides a shape memory alloy structure extending along a longitudinal axis and having a retracted state and a deployed state. The structure includes a tubular member including a plurality of substantially solid, concave outer surface panels forming the tubular member circumference. Each panel is coupled to two adjacent panels on opposed sides at peak portions at radially outermost portions of the tubular member in the deployed state. Each panel extends substantially parallel to the prosthesis's longitudinal axis, and wherein the retracted state has the panels and the peak portions of the tubular member positioned radially inwardly of their respective positions in the deployed state and the retracted state has each panel bending about an axis parallel to the longitudinal axis forming generally greater outer surface concavity than in the deployed state, whereby a substantially tight serpentine structure is formed by the panels and peaks in the retracted state.

The invention provides a shape memory alloy structure extending along a longitudinal axis and having a retracted state and a deployed state, said structure comprising: an outer tubular member including a plurality of substantially solid, concave outer surface panels forming the tubular member circumference, each panel coupled to two adjacent panels on opposed sides at peak portions at radially outermost portions of the tubular member in the deployed state, and wherein each panel extends substantially parallel to the prosthesis's longitudinal axis; and an inner tubular member including a plurality of substantially solid convex inner surface panels forming the circumference of the inner tubular member, each panel coupled to two adjacent panels on opposed sides at peak portions at radially outermost portions of the tubular member in the deployed state, and wherein each panel extends substantially parallel to the prosthesis's longitudinal axis; and wherein the inner tubular member peaks are coupled to the outer tubular member peaks, and wherein central portions of the inner tubular member panels are spaced from the central portions of the outer tubular member panels.

It is noted that, as used in this specification and the appended claims, the singular forms "a," "an," and "the" include plural referents unless expressly and unequivocally limited to one referent. The features that characterize the present invention are pointed out with particularity in the claims which are part of this disclosure. These and other features of the invention, its operating advantages and the specific objects obtained by its use will be more fully understood from the following detailed description and the operating examples. These and other advantages of the present invention will be clarified in the brief description of the preferred embodiment taken together with the drawings in which like reference numerals represent like elements throughout.

BRIEF DESCRIPTION OF THE DRAWINGS

FIGS. 9A and 9B are partial section views of a folding fixture for collapsing a lightweight, collapsible, shape memory alloy structure according to the present invention;

FIGS. 10A-D are partial section views of a further folding fixture for collapsing a lightweight, collapsible, shape memory alloy structure according to the present invention;

DESCRIPTION OF THE PREFFERED EMBODIMENTS

Figure 1A:
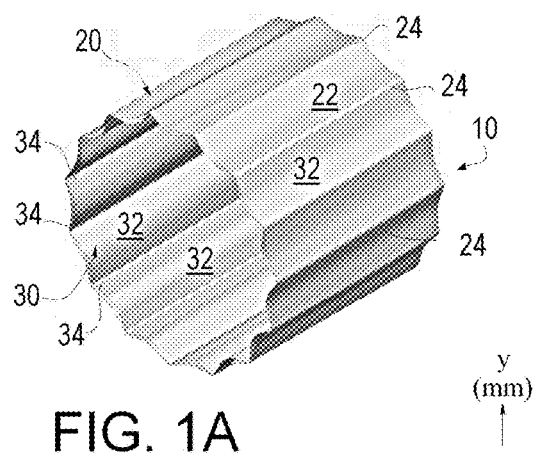
FIGS. 1A and 1B are perspective views of a lightweight, collapsible, shape memory alloy structure in the form of a collapsible lumen in accordance with one embodiment of the present invention.
Figure 1B:
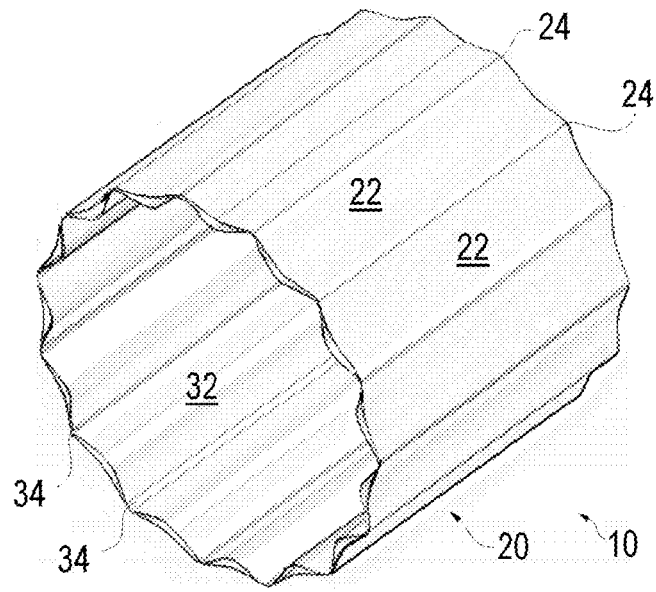

The present invention provides a shape memory alloy structure 10 that may include at least two layers 20 and 30 formed of shape memory material, such as NiTI-based alloys including nitinol. As described in further detail herein the structure 10 can have numerous applications. FIGS. 1A and 1B perspective views of a lightweight, collapsible, shape memory alloy structure 10 in the form of a collapsible lumen that can form for example a medical stent in accordance with one embodiment of the present invention. Other configurations and applications are possible without departing from the scope of the present invention and only a few representative examples will be discussed herein.

The collapsible lumen of structure 10 of FIGS. 1A and B is helpful to illustrate the particulars of the present invention. The phrase collapsible is used herein to reference a change in shape of the alloy structure 10 typically to accommodate the application or deployment of the structure 10 to its operative location. It is anticipated that the operative condition of the structure 10 may in some applications actually be the retracted position, such as for example where the alloy structure 10 is a lumen designed to approximate valve leaflets towards a closed position, thus the term collapsible is not intended to define the operative condition of the structure 10. As described in detail below one advantageous property of the lumen or tubular shaped structure 10 is that it moved between the retracted or collapsed stated and the expanded state without changing length. This feature increases the ability of the users to precisely place the structure 10, such as when formed as a stent or valve in medical application or a filter support in remote placement applications, into its operational position as will become more apparent in the following description.

As noted the structure 10 of FIGS. 1A and B includes two layers 20 and 30, an inner layer 30 and an outer layer 20. Each layer 20 and 30 is formed with the structure in the expanded position as shown in FIGS. 1A and B as including a plurality of concave or scalloped panels 22 and 32 each having side edges forming peaks 24 and 34. The phrase "side edges" is not intended to set forth a sharp "edge" but merely the lateral ends of the panel 22 or 32 on either side thereof, as in practice there is a blending of the radii as the surface moves from the panel 22 or 32 to the relatively sharp radii of "convex" peaks 24 and 34.

The present invention provides that at least some, if there are more than two layers 20 and 30 in structure 10, of the adjacent layers 20 and 30 are coupled together via a filler material such as a niobium (Nb) metal, at selected edges of adjacent panels. The filler material may be a niobium braze material such as disclosed in U.S. Pat. No. 7,896,222, which is incorporated herein by reference. As further detailed in the '222 patent niobium based braze material may be implemented as a liquid reactive braze material, for fabrication of "cellular" or "honeycomb structures", wire space-frames or other "sparse" built up structures or discrete articles using Nitinol and related shape-memory and super-elastic alloys. The braze process is properly summarized as a reactive eutectic brazing process using Nb as a melting point depressant for nitinol. The Niobium brazing material when brought into contact with Nitinol at elevated temperature, liquefies at temperatures below the melting point and flows readily into capillary spaces between the elements to be joined, thus forming a strong joint. This Niobium based brazing material, such as pure niobium and niobium alloys, and the associated coupling techniques are well suited for coupling the layers 20 and 30 of the structure 10 at adjacent peaks 34 and 24.

Regarding the Niobium containing brazing material and associated brazing methods see also U.S. Patent publication numbers 2011/0009979, 2011/0008643, and 2008/0290141 which are incorporated herein by reference. Regarding general background for similar couplings see also "Transient Liquid Phase Bonding", MacDonald et al., 1992, Annu. Rev. Mater. Sci. 22:23-46; "Transient Liquid Phase (TLP) Diffusion Bonding of a Copper Shape Memory Alloy Using Silver as Interlayer", DeSalazar et al., Scripta Materialia, vol. 37, No. 6, pp. 861-867, 1997. It is noted, however, that the title of these articles may be somewhat misleading as to the present process described in U.S. Patent publication numbers 2011/0009979, 2011/0008643, and 2008/0290141, wherein the braze process is properly summarized as a reactive eutectic brazing process using Nb as a melting point depressant for nitinol, and not a "transient liquid" bonding process as the term "transient liquid" is sometimes used.

The joining technique using niobium based filler for coupling peaks 24 and 34 may be a "spot-welding" technique for the shape-memory alloy layers 20 and 30 using conventional resistance-welding techniques. For example, a thin foil of pure niobium is placed between the peaks 24 and 34 to be joined. Thereafter, under appropriate clamping pressure, an electrical current pulse is passed through the coupled peaks 24 and 34 with sufficient intensity to cause transient melting. The spot welding technique can be used to hold complex structures together prior to the full brazing process described herein to avoid the necessity to use elaborate fixtures or jigs. A schematic brazing fixture is discussed in connection with FIG. 6D which can assist in the process allowing all couplings to be made at once.

The adhering process using niobium based filler can include metal-inert gas (MIG) welding of shape-memory alloys of the peaks 24 and 34 wherein, for example, a pure niobium welding wire is fed into the welding arc which is shielded by an appropriate flow of inert gas. The same principles of flux-less processing, eutectic liquid formation, and the formation of ductile, biocompatible solidification products associated with the Niobium brazing process applies to this MIG method of joining layers 20 and 30.

For small scale structures 10, such as used for medical stents and valves, the filler metal, such as niobium and niobium alloys, may sputtered onto at least some of the edges or peaks 24 and 34 to allow for thin film application associated with these applications. It will likely be applied to only one of the two surfaces to be joined, whichever presents the easier application surface. Sputtering is a preferred method for placing niobium when the amount needed is less than can be provided by a wrought niobium foil. The method of forming the shape memory alloy structure 10 may further provide that the sputtering step of applying niobium to the selected edges or peaks 24 and 34 of the layers 20 and 30 includes the use of mask members to control the application of the niobium filler material to only the designated desired area. In essence such masks will cover those areas of the layer 20 or 30 not to be sputtered with the filler material. Other methods of filler material application include vacuum evaporation, plasma deposition or kinetic spray techniques, some of which may prove to be particularly efficient and cost effective.

The filler material as discussed above may be referenced as a brazing material a welding material or even a soldering material. Preferably the filler material is pure niobium or niobium alloyed with any metal capable of forming an alloy with niobium. Niobium composite structures are also possible with multilayer foils.

Figure 2:
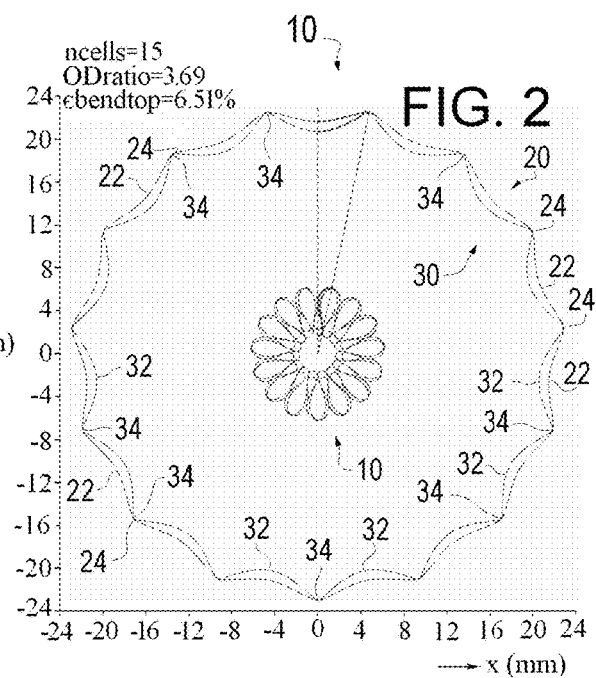
FIG. 2 is a graphical schematic representation of the collapse and expanded states of the lightweight, collapsible, shape memory alloy structure of FIGS. 1A and 1B.

Returning to the FIGS. 1A and B, the structure 10 is moveable between a contracted position shown schematically in FIG. 2 and an extended position shown in FIGS. 1A and B wherein the coupled edges or peaks 34 and 24 essentially form hinges as shown for moving the structure 10 between the contracted position and the extended position. As noted FIG. 2 is a graphical schematic representation of the collapse and expanded states of the structure 10 of FIGS. 1A and 1B. The scalloped panels 22 and 32 and the peaks 24 and 34 allow for the unique compaction demonstrated in FIG. 2. This collapsing design as shown allows for a wide variety of expanding/contracting structures to be designed, including wherein the structure 10 is moveable between a radially contracted position and a radially extended position, wherein the effective outer diameter of the structure in the radially extended position is at least twice, at least three times, at least three and one half times or even 3.8 times in the example shown, of the effective outer diameter of the structure in the radially contracted position. Thus for example the effective outer diameter of the structure 10 in the radially contracted position as shown is less than about 6 mm, allowing for the structure to effectively form medical devices such as inner lumen delivered stents and valves in medical applications.

Figure 3A:
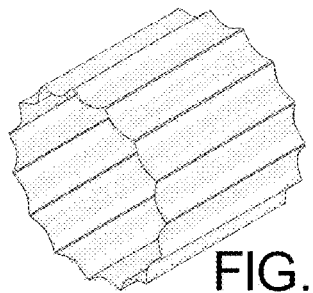
FIG. 3A is a perspective view of one layer of the lightweight, collapsible, shape memory alloy structure of FIGS. 1A and 1B.
Figure 3B:
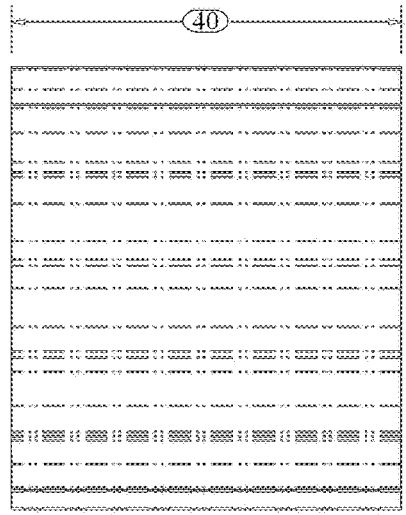
FIG. 3B is a schematic side elevation view of the layer of FIG. 3A.
Figure 3C:
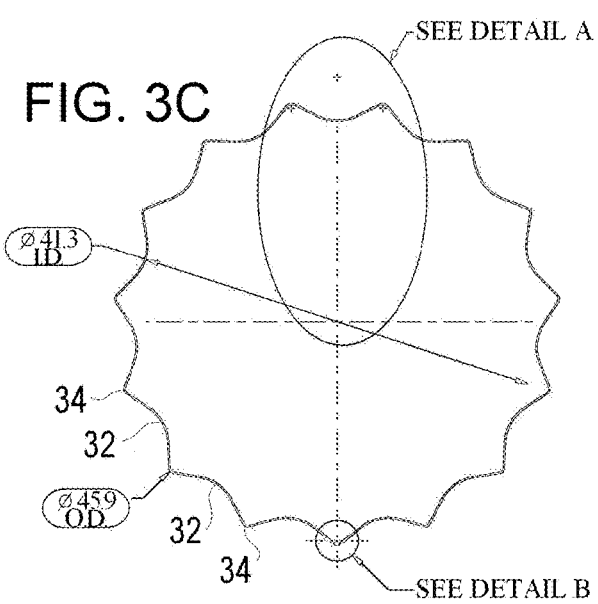
FIG. 3C is a schematic end view of the layer of FIG. 3A.
Figure 3D:
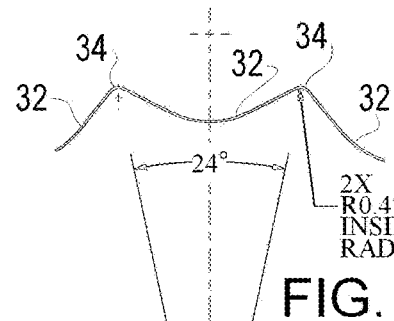
FIG. 3D is an enlarged schematic end view of circumferentially adjacent scalloped panels of the layer of FIG. 3A.
Figure 5:
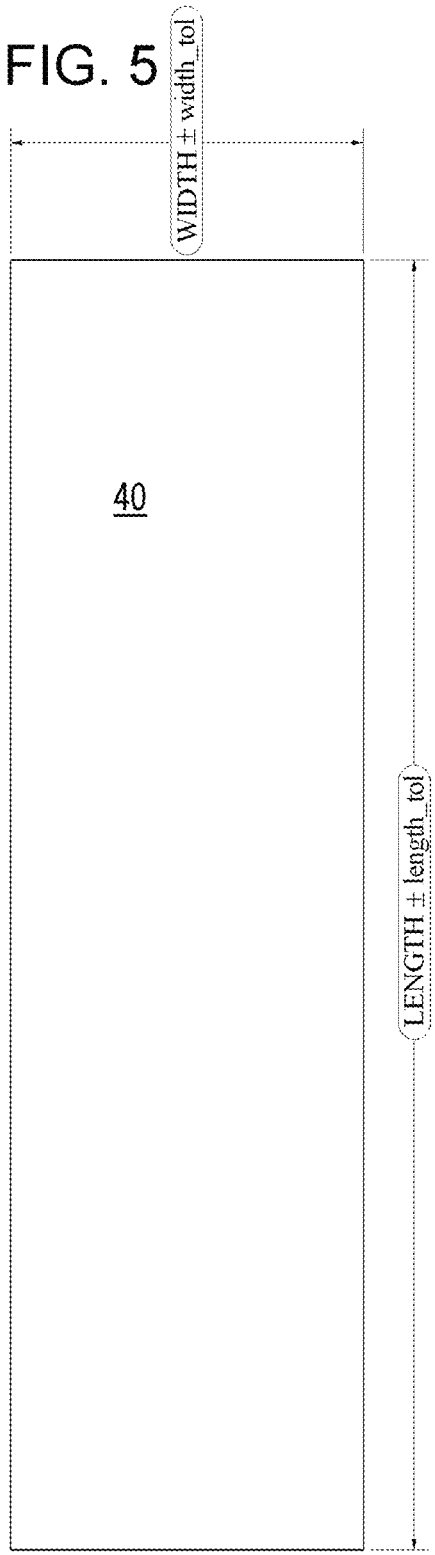
FIG. 5 is a plan view of a shape memory alloy sheet used to form each of the layers of the lightweight, collapsible, shape memory alloy structure of FIGS. 1A and 1B.

Turning to FIGS. 3A-E, FIG. 3A is a perspective view of one layer 30, the inner layer 30, of the lightweight, collapsible, shape memory alloy structure 10 of FIGS. 1A and 1B. As noted above more than two layers 20 or 30 can be used to form the structure 10. FIG. 3B is a schematic side elevation view of the layer 30 of FIG. 3A; while FIG. 3C is a schematic end view of the layer 30 of FIG. 3A showing the undulating scalloped pattern of panels 32 and peaks 34. FIG. 3O is an enlarged schematic end view of circumferentially adjacent scalloped panels 32 of the layer 30 with intermediate peaks 34. The layer 30 is formed of a shape memory alloy as noted such as a sheet 40 of nitinol shown in FIG. 5. FIG. 5 is a plan or top view of a shape memory alloy sheet 40, such as a NiTi-alloy sheet used to form each of the layers 20 and 30 of the lightweight, collapsible, shape memory alloy structure 10 of FIGS. 1A and 1B.

Figure 3E:
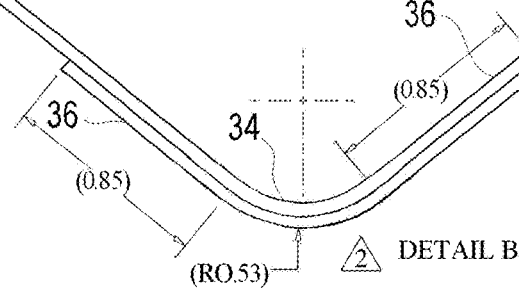
FIG. 3E is an enlarged schematic end view of coupling of ends of the layer of FIG. 3A to form the collapsible lumen.

When formed into the undulating shape with scalloped panels 32 and peaks 34 the ends 36 of the sheet 40 will overlap at some section and the overlapping ends 36 can be coupled together in the same fashion as the adjacent aligned peaks 34 and 24 discussed above. FIG. 3E is an enlarged schematic end view of coupling of overlapped ends 36 of the layer 30 of FIG. 3A to form the lumen layer 30 for the structure 10. As discussed above, a niobium filler material such as in a braze material can couple ends 36. The length of overlap of ends 36 may be minimized, or may alternatively be positioned on a panel 32. However the peak 34 placement of the overlapped ends 36 may assist in securing the ends 36 together throughout operation of the structure 10. An alternative configuration is to align the ends 36 next to each other and butt weld (with Niobium based welding material, for example) the edges of these ends 36 to avoid a double thickness portion, but the overlapped ends 36 as shown is generally believed to be more easily manufactured.

Figure 4A:
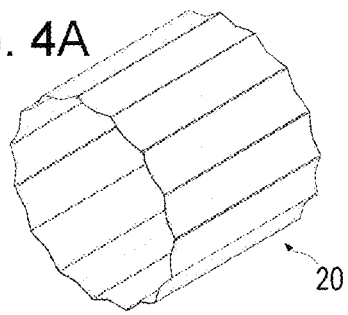
FIG. 4A is a perspective view of the second layer of the lightweight, collapsible, shape memory alloy structure of FIGS. 1A and 1B.
Figure 4B:
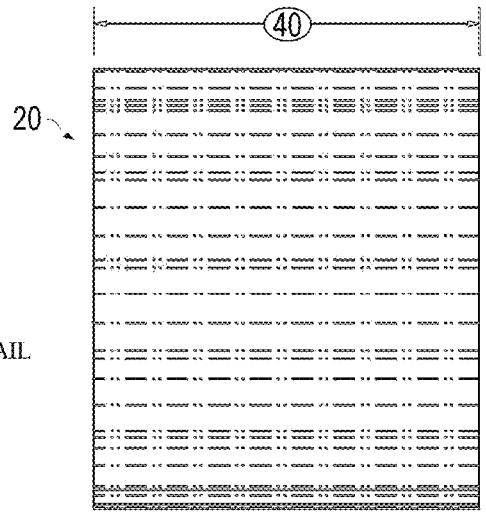
FIG. 4B is a schematic side elevation view of the layer of FIG. 4A.
Figure 4C:
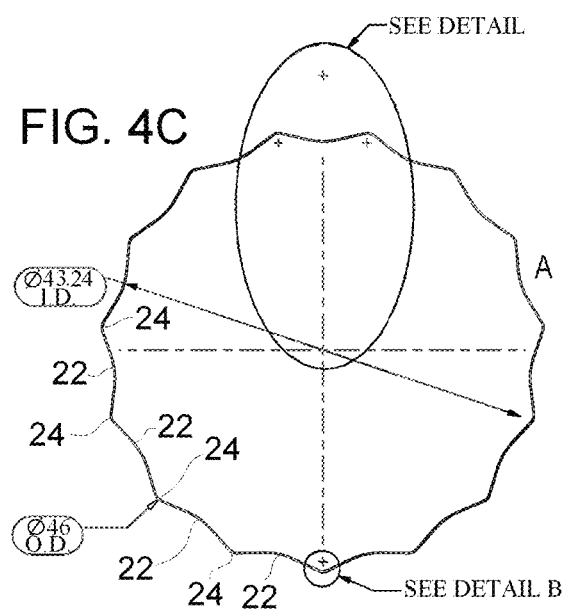
FIG. 4C is a schematic end view of the layer of FIG. 4A.
Figure 4D:
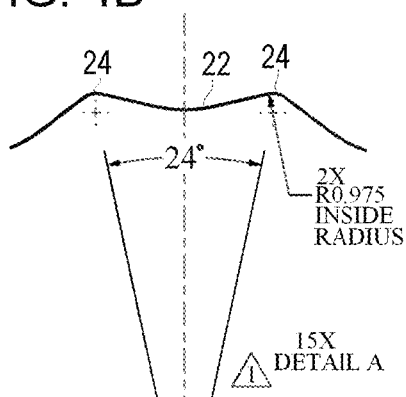
FIG. 4D is an enlarged schematic end view of circumferentially adjacent scalloped panels of the layer of FIG. 4A.
Figure 4E:
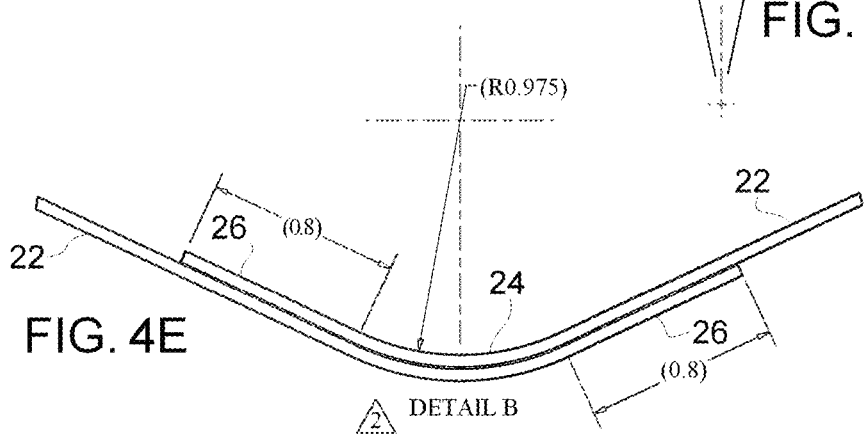
FIG. 4E is an enlarged schematic end view of coupling of ends of the layer of FIG. 4A to form the lumen.

Turning to FIGS. 4A-E, which are analogous to FIGS. 3A-E, FIG. 4A is a perspective view of one layer 20, the outer layer 20, of the lightweight, collapsible, shape memory alloy structure 10 of FIGS. 1A and 1B. More than two layers 20 or 30 can be used to form the structure 10, and in an alternative configuration only a single layer 20 or 30 may form the structure. FIG. 4B is a schematic side elevation view of the layer 20 of FIG. 4A; while FIG. 4C is a schematic end view of the layer 20 of FIG. 4A showing the undulating scalloped pattern of panels 22 and peaks 24. FIG. 4D is an enlarged schematic end view of circumferentially adjacent scalloped panels 22 of the layer 20 with intermediate peaks 24. The layer 20 is formed of a shape memory alloy as noted such as the sheet 40 of nitinol shown in FIG. 5. When formed into the undulating shape with scalloped panels 22 and peaks 24 the ends 26 of the sheet 40 will overlap as shown in FIG. 4E at some section and the overlapping ends 26 can be coupled together in the same fashion as ends 36 discussed above.

Figure 6A:
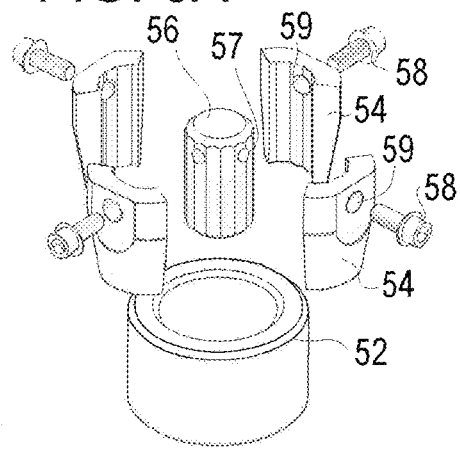
FIG. 6A is an exploded view of a formation fixture for forming each layer of the lightweight, collapsible, shape memory alloy structure of FIGS. 1A and 1B.
Figure 6B:
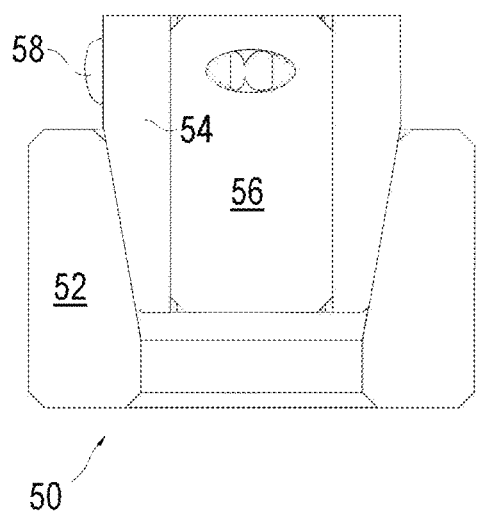
FIG. 6B is a sectional schematic view of the formation fixture of FIG. 6A for forming each layer of the lightweight, collapsible, shape memory alloy structure of FIGS. 1A and 1B.

FIG. 6A is an exploded view of a formation fixture for forming each layer 20 or 30 of the lightweight, collapsible, shape memory alloy structure 10 of FIGS. 1A and 1B from the individual NiTi sheets 40 of FIG. 5. FIG. 6B is a sectional schematic view of the formation fixture of FIG. 6A. As shown a simple formation fixture can include an annular base 52 receiving a plurality of outer dies or molds or bending forms 54 that have an inner surface matching the desired shape of the panels 32 or 22 and peaks 24 or 34 of layers 20 or 30. The forms 54 surround a core 56 having an outer surface matching the desired shape of the panels 32 or 22 and peaks 24 or 34 of layers 20 or 30. The forms 54 includes alignment holes 59 therein that will align with holes 57 in core for receipt of aligning pins or bolts 58. The threading of holes 57 allows the bolts 58 to be tightened to clamp down on an intervening sheet 40. Placing sheet 40 into the fixture of FIGS. 6A and 6B allows the sheet 40 to be formed in the desired configuration shown for layers 20 and 30. Heat treating of the sheet in fixture 40 may be used to set the shape of the shape memory alloy as known to those of ordinary skill in the art.

Figure 6C:
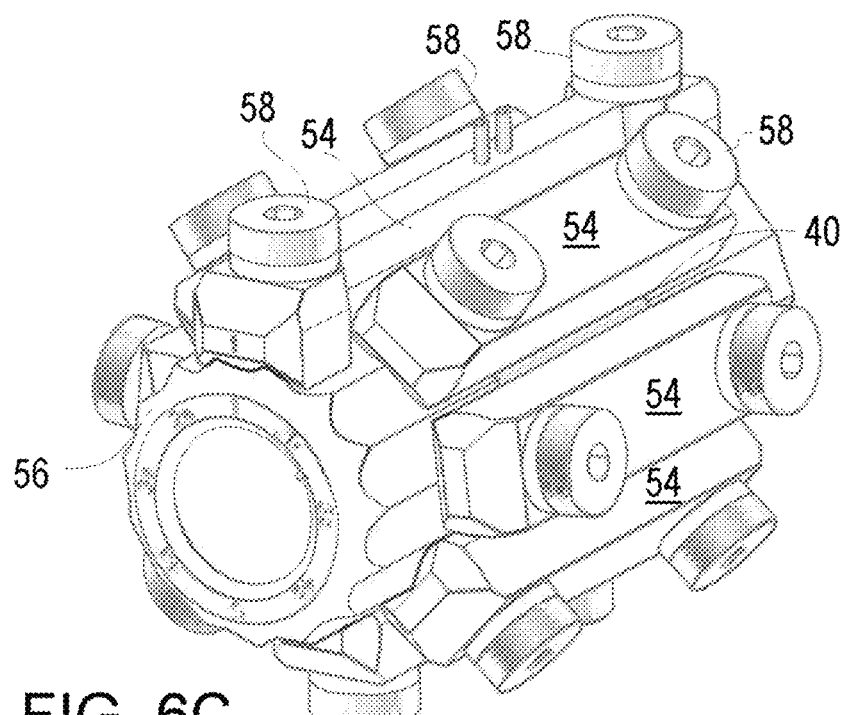
FIG. 6C is a perspective schematic view of an alternative formation fixture for forming each layer of the lightweight, collapsible, shape memory alloy structure of FIGS. 1A and 1B.

FIG. 6C is perspective view of a formation fixture for forming each layer 20 or 30 of the lightweight, collapsible, shape memory alloy structure 10 of FIGS. 1A and 1B from the individual NiTi sheets 40 of FIG. 5. The concept is somewhat similar to the formation fixture of FIGS. 6A and B. As shown a simple formation fixture can include a plurality of outer dies or molds or bending forms 54 that have an inner surface matching the desired shape of the panels 32 or 22 and peaks 24 or 34 of layers 20 or 30. The forms 54 surround a core 56 having an outer surface matching the desired shape of the panels 32 or 22 and peaks 24 or 34 of layers 20 or 30. The forms 54 includes alignment holes (analogous to holes 59 above) generally on opposed sides of the sheets 40 in the fixture, and the holes in forms 54 will align with holes (analogous to holes 57 above) in core 56 for receipt of aligning pins or bolts 58. The threading of holes in core 56 allows the bolts 58 to be tightened to clamp down on an intervening sheet 40. Placing sheet 40 into the fixture of FIG. 6C, like FIGS. 6A and 6B, allows the sheet 40 to be formed in the desired configuration shown for layers 20 and 30. Heat treating of the sheet in fixture 40 may be used to set the shape of the shape memory alloy as known to those of ordinary skill in the art.

Figure 6D:
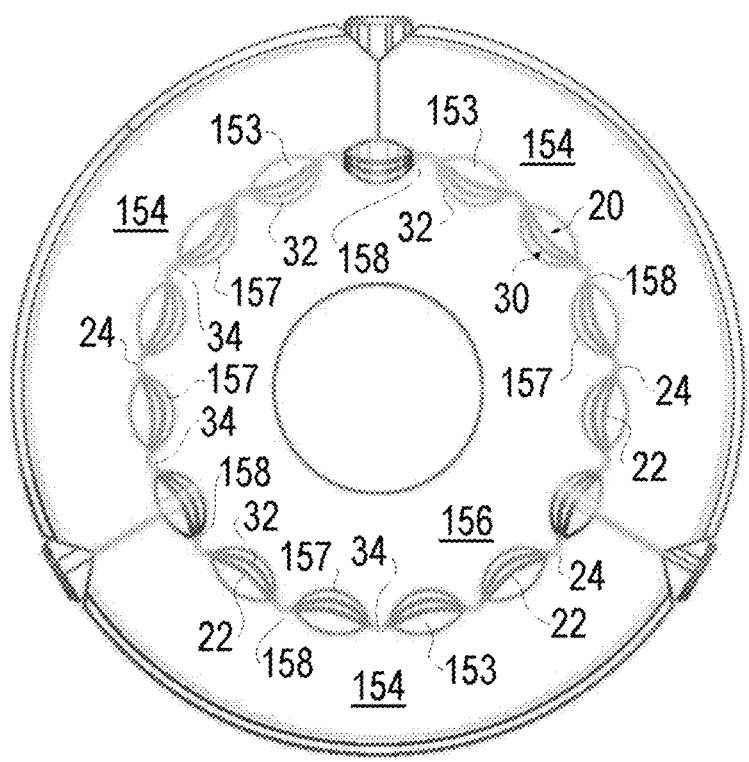
FIG. 6D is a sectional schematic view of a brazing fixture for completing the brazing attachment of the layers of the lightweight, collapsible, shape memory alloy structure of FIGS. 1A and 1B.

FIG. 6D is section schematic view of a brazing furnace fixture for forming the lightweight, collapsible, shape memory alloy structure 10 of FIGS. 1A and 1B from the individual NiTi layers 30 and 20. The furnace fixture concept of FIG. 6D is somewhat similar to the formation fixture of FIG. 6C. As shown a brazing fixture can include a plurality of outer clamping member forms 154 that have an inner surface matching the desired shape peaks 24 and 34 of layers 20 and 30, with open recesses 153 aligned with panels 22 and 32 of layers 20 and 30. The forms 154 surround a core 156 having an outer surface matching the desired shape peaks 24 and 34 of layers 20 and 30, with open recesses 157 aligned with panels 22 and 32 of layers 20 and 30. The forms 154 and core 156 may be bolted together in the same manner as the fixtures of FIGS. 6A-C.

Placing layers 20 and 30 into the fixture of FIG. 6D with the brazing material located at the peaks 24 and 34 and placing the fixture into an associated furnace allows the brazing to be completed to form the structure 10. The furnace fixture as shown would be made out of material appropriate for withstanding furnace application for completing the brazing. In short the furnace fixture of FIG. 6D will clamp the peaks 24 and 34 together for the brazing operation while the recesses 153 and 157 accommodate and are spaced from the panels 32 and 22. It may be desirable to have the fixture fabricated primarily from Tungsten, Molybdenum, Inconel, or possibly Nitinol itself. Additionally portions that are non-contact elements may be made from stainless steel. As shown the clamping fixture effectively limits contact to that along the single braze lines at the peaks 22 and 34 and may further be longitudinally limited to only the last 10% or so on each side (i.e. ends of the fixture). The "furnace fixture" of FIG. 6D could also possibly serve as an electrical spot welding fixture with the inclusion onto the surfaces of the forms 154 and core 156 of electrical couplings or leads 158 that, because of the recesses 153 and 157 will contact only the layers 20 and 30 and only at the desired brazing lines at the peaks 24 and 34.

Placing layers 20 and 30 into the spot welding fixture with the brazing material located at the peaks 24 and 34 allows the brazing to be completed to form the structure 10, whereby, under appropriate clamping pressure, an electrical current pulse is passed through the coupled peaks 24 and 34 with sufficient intensity to cause desired melting.

The radii at peaks 24 and 34 and the other radii forming panels 22 and 32 are blended to form a continuous curvature. The peaks 24 and 34 are generally formed with minimal radii as reasonable while the various radii of the panels 32 and 22 depend upon the desired number of panels 22 and 32, the desired size of the inner lumen formed by panel 32 and the desired size of the channels formed between the panels 22 and 32 and the diameter of the contracted position with a given size for the nitinol forming each layer 20 or 30. The response characteristics desired can also be used in the design for selecting particular radii. The illustrated structures 10 are intended to be representative and not restrictive or limiting of the relative shapes of the panels and peaks of layers 20 and 30.

Figure 7A:
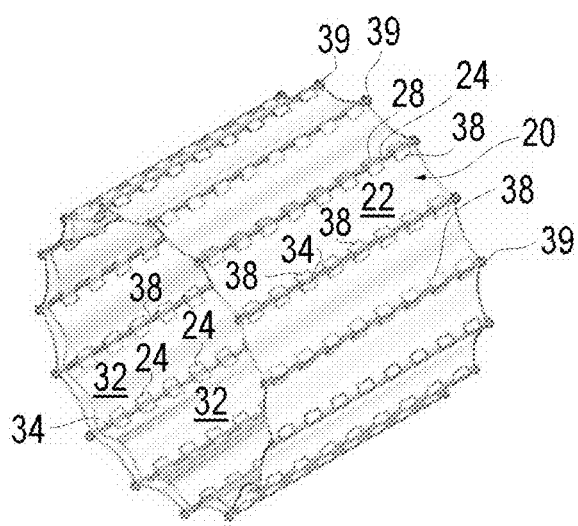
FIG. 7A is a perspective view of an alternative lightweight, collapsible, shape memory alloy structure in accordance with another embodiment of the invention.
Figure 7C:
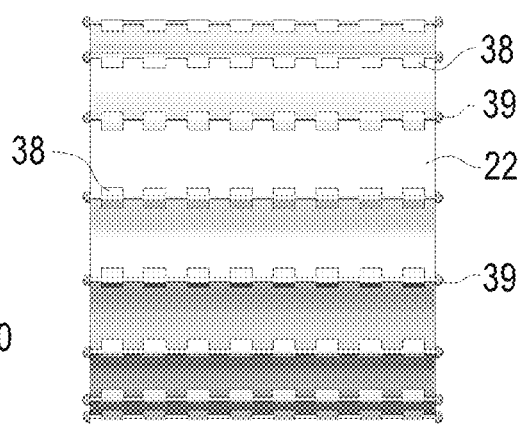
FIG. 7C is a schematic side elevation view of the lightweight, collapsible, shape memory alloy structure of FIG. 7A.
Figure 7B:
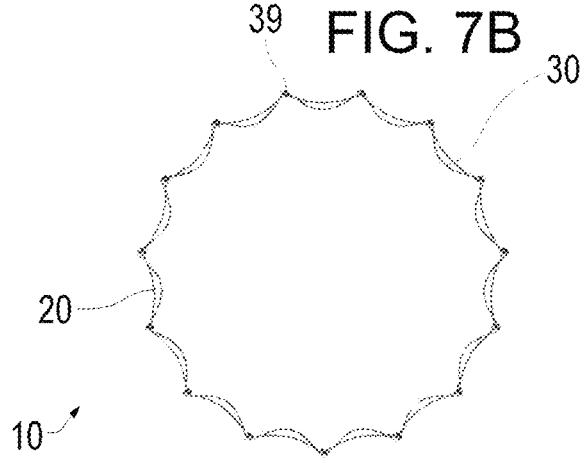
FIG. 7B is a schematic end view of the lightweight, collapsible, shape memory alloy structure of FIG. 7A.
Figure 7D:
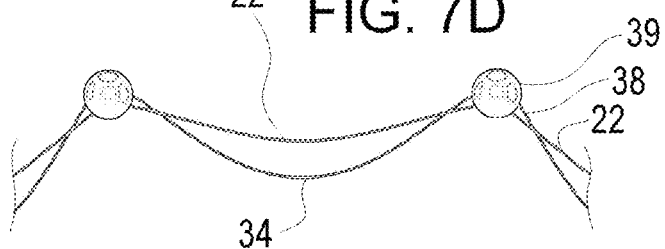
FIG. 7D is an enlarged schematic end view of circumferentially adjacent scalloped panels of the lightweight, collapsible, shape memory alloy structure of FIG. 7A.

FIGS. 7A-D illustrates an alternative lightweight, collapsible, shape memory alloy structure 10 in accordance with another embodiment of the invention. FIG. 7A is a schematic perspective view of the lightweight, collapsible, shape memory alloy structure 10; FIG. 7B is a schematic end view of the structure 10; FIG. 7C is a schematic side elevation view the structure 10 and FIG. 7D is an enlarged schematic end view of circumferentially adjacent scalloped panels 22 and 32 of the lightweight, collapsible, shape memory alloy structure 10 of FIG. 7A. The difference in these figures from earlier described embodiments is the elimination of the filler material, such as the niobium braze, coupling the layers 30 and 20. In this embodiment the peaks 24 includes openings 28 that receive corresponding leaves 38 of aligned peak 34 that can receive an interlocking pin 39 to couple the adjacent layers 20 and 30 at peaks 24 and 34. This embodiment is to illustrate alternative "braze-less" coupling techniques for layers 20 and 30. Alternative mechanical couplings can be implemented.

The tubular multilayer structure 10 shown in FIGS. 1A-B can be used in a variety of applications. For example structure 10 is effective, essentially as shown, as a biomedical stent. In the medical field a stent is an artificial 'tube' inserted into a natural lumen or passage or conduit in the body to prevent, or counteract, a localized flow constriction. The term can also refer to a tube used to temporarily hold such a natural lumen open or to create a lumen or passage to allow access for surgery, in other words to act as a tubular retractor or conduit for medical procedures (and similar devices are used in non-medical procedures).

Figure 14:
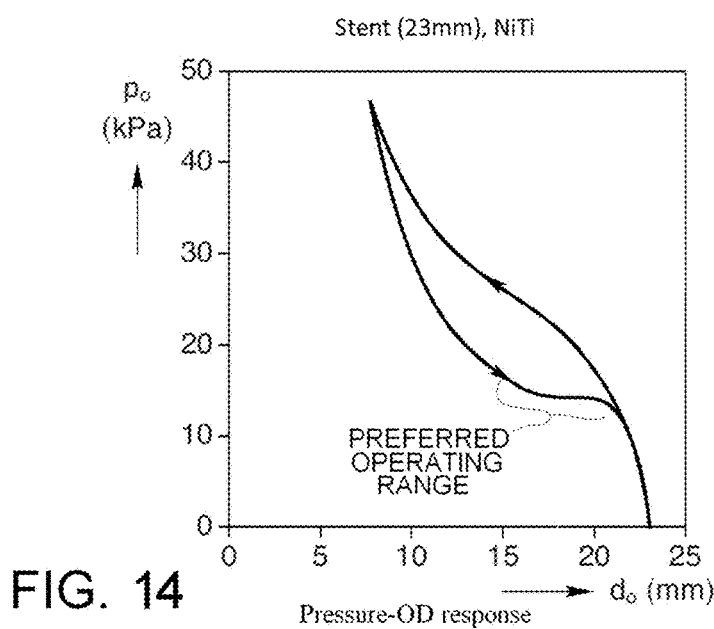
FIG. 14 is a response curve illustrating the pressure exerted over a range of outer diameter sized for a lightweight, collapsible, shape memory alloy structure formed according to the present invention.

The structure 10 of the present invention has exceptional response curve shown in FIG. 14, namely a "flatter" response over radial constriction that can allow a single size structure to be utilized over a wider range of applicable lumen sizes than prior art stent designs. In other words a more constant radial force is exhibited over a wider deformation than can be found in prior art stent designs. This advantageous result is believed to also be present to a lesser degree with only a single layer 20 or 30. The multi-layer structure as shown increases this advantageous characteristic.

FIG. 14 is a graph of a response curve illustrating the pressure exerted by a structure 10 over a range of outer diameter sized for a lightweight, collapsible, shape memory alloy structure 10 formed according to the present invention as a 23 mm outer diameter structure 10 formed as the device shown in FIG. 1A. The graph illustrates a fully expanded size of 23 mm and a preferred operating range for constant pressure. A simple increase in the diameter of the structure 10, which may be a stent, would shift the black recoverable curve to the right, allowing, for example, the intersection points of the 18 mm and 22 mm lines to be essentially in the plateau of the black curve. This characteristic of the structure 10 when applied to a stent would make the applied force of the structure within the designated range of operation relatively constant throughout multiple size vessels irrespective of the age of the patient. This gives the structure 10 the ability to effectively stay in contact with a continuously changing diameter of the associated lumen within which the structure 10 is placed (such as in a stent application and the diameter change being due to pulsatility found in the human body). Because of the constant outward force over a wide range of diameters in the preferred operating range, the structure 10 of the present invention will stay in contact with a vessel that is changing sizes.

As noted, the static axial length of the structure 10, as a stent in particular, offers a distinct operational advantage in that there is a much higher degree of certainty in the device 10 placement due to the static axial length between radially different positions. Further when implemented as a stent the device 10 of the invention differs from conventional "self-expanding stents" that generally consist of a single layer of NiTi and are commonly laser-cut from tubes which is associated with an unfavorable crystallographic texture in the circumferential direction. Further unlike device 10, conventional stents typically rely on ligaments that bend within the cylindrical surface of a virtual tube (having surface normal in the radial direction) wherein, by contrast, the device 10 described herein allows the possibility of metallurgically-bonded corrugations and/or honeycombs, so-called thin-walled "cellular" structures. It should be evident from the description that this cellular structure is not to be confused with "porous" SMAs which do not have regular, periodic structures and are not thin-walled). In contrast with conventional stent designs the structure 10 allows construction of the device from wrought NiTi elements that have improved mechanical properties and transformation strain (with a more favorable texture), and can employ bending within the "tube" cross-section (with normal in the axial, z-direction). These advantages extend beyond the stent field, but the stent field allows for easy comparison of the present structure 10 to conventional construction.

The "stent" concept is not limited to medical applications but can be used for opening and holding-open other restricted lumens, or creating a lumen or passageway in industrial applications, e.g., a crimped fuel line can be internally reinforced with the structure 10 allowing reinforcement without taking the system off line and disassembling the device, which may be particularly advantageous for complex machinery; or a flexible vent tube of a machine may be held in an expanded state for access of an inspection scope. Another representative application is using the structure 10 as a base for an internal filter structure such as to contain emboli in medical applications or unwanted particulate matter in general applications. A filter sack or filtering material would be extended across the inner surface of the outer layer 20 such as at the down-stream end to contain the emboli within the structure 10. The structure 10 could be later removed, such as in distal protection filters used in angioplasty and stent placement. In industrial applications, it could be used in a fuel or hydraulic fluid line downstream of a filtering assembly that is being replaced or otherwise serviced. Another representative application is using a shortened version of structure 10 as an expanding membrane that can used to occlude a defect.

The shape of the multi-layer structure 10 as shown has other advantages, as illustrated the adjacent panels 32 and 22 of adjacent layers 20 and 30 form channels between the layers 20 and 30. These channels can be used in medical applications for onsite drug delivery purposes. Specifically one or more medicaments may be placed within selected channels to be delivered in situ. For example an anticoagulant or anti thrombotic medicament may be included in channels of a stent formed from the structure 10. The types of medicaments are not limited and there can be as many distinct types as channels. Additionally, for medical applications the surfaces of the layers 20 and 30 may be surface treated or coated to provide medicaments or desired biomolecule, such as heparin coated on the inner surface of inner layer 30 for a stent application. The outer surface of outer layer 20 may have a distinct bio-coating or surface treatment particular to its application, and the inside of the channels may have a third surface treatment or coating. The coatings or surface treatments may be in addition to the packing or filling of the channels with medicaments as discussed above. The filling of the channels with material to be dispensed when the structure is positioned is only limited in that the channel must not be filled too much so as to interfere with moving from a retracted state to the deployed state. The channels could also serve as effective location for other elements, such as the positioning of nanotechnology or nanomachines, such as for example the NANOPUMP™ brand of Debiotech's miniaturized drug delivery pumps.

As noted the shape memory alloy structure 10 according to the present invention may have an outer facing surface of an outermost of the layer with a distinct surface treatment or coating from an inner facing surface of an innermost of the layers. This concept of different structuring can include different surface finishes on the inner and outer layers 20 and 30. For example, the shape memory alloy structure 10 according to the invention may have one of the outer facing surface of the outermost of the layers 20 and the inner facing surface of the innermost of the layers 30 be substantially uniformly perforated and the other be substantially solid. In an alternative arrangement one surface may have a textured surface for attachment wherein the other surface is intentionally smooth. Alternatively, different alloys (having different transformation temperatures) for the inner and outer sheets 20 and 30 may be utilized, to provide, for example, an increase in the temperature range of functionality, or to control the plateau characteristics of the stress-strain behavior of the resulting structure 10 discussed in connection with FIG. 14. In a further alternative, the two layers 20 and 30 could also be of different thickness to provide the desired operating characteristics of the structure 10. The multi-layer construction of structure 10 allows these differing constructions to be more easily accommodated than other nitinol structures such as existing medical stent designs.

Figure 8:
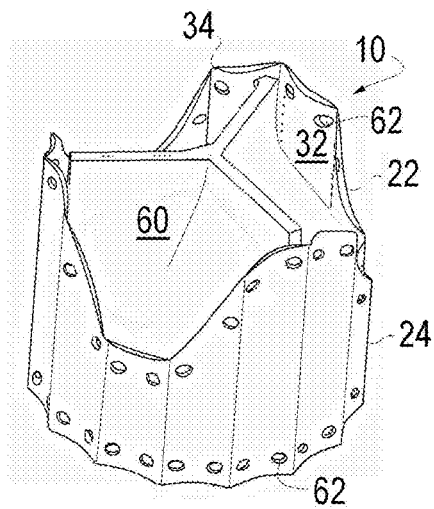
FIG. 8 is a perspective view of a heart valve formed with the lightweight, collapsible, shape memory alloy structure according to the present invention.

The multi-layer construction of structure 10 according to the present invention is applicable for many biologic applications in humans and animals with medical stents and filters as discussed above being two easily understood implementations. A heart valve 60 as shown in FIG. 8 represents another important implementation of the present invention. FIG. 8 is a perspective view of a heart valve 60 formed with the lightweight, collapsible, shape memory alloy structure 10 according to the present invention. Leaflet valve members are coupled to the inner layer 30 panels 32 forming the valve. The structure 10 can include a number of preformed suture openings 62 for securing the valve 60 in place. The construction of the leaflets is known in the art and not discussed further herein as this is merely to illustrate another implementation of the present structure 10. The valve structure 60 may be a more general medical valve, such as various body sphincters—gastric, urinary, or rectal as examples. The collapsing and expanding characteristic of the structure 10 makes it particularly beneficial for medical valve applications; however the valve as shown need not be used in a medical application.

Other representative medical applications that the structure 10 of the present invention may be useful in forming include atrial septal defect prosthesis, orthopedic pins, rods, plates, anchors and screws, auditory implants (such as portions of a cochlear implant), nasal implants, urinary tract implants, tear duct implants, and esophageal implants. This is not an exhaustive list, merely intending to show the wider application of the structure 10.

In many medical implant procedures for implanting a device, such as valve 60, the device must be collapsed to its retracted position on site and not pre-loaded. Pre-loading is referencing a collapsing of the device at the manufacturer and shipping it to users in the retracted condition within a deployment vehicle. In many applications it is desired to maintain the structure 10 in the expanded condition till immediately prior to deployment and then, on site, collapse the structure and load it into a delivery vehicle, such as a catheter. For these applications there is a need for simple collapsing or folding fixtures to allow for easy "loading" of the device on site. Existing folding fixtures for nitinol medical devices have been overly complex.

The structure 10 of the present invention allows for a greater simplicity in suitable on site folding fixtures than many other existing nitinol folding fixtures. FIGS. 9A and 9B are partial section schematic views of a folding fixture 70 for collapsing a lightweight, collapsible, shape memory alloy structure 10 according to the present invention. The fixture 70 is formed of a body member 72 with an inlet opening 74 of a first diameter at one end thereof configured to receive the expanded structure 10 therein and a smaller diameter outlet 78 at an opposite end thereof of a diameter associated with the desired loading diameter for the structure 10. A converging surface 76 extends between the inlet opening 74 and the outlet opening 78. The operator merely manually passes the collapsible shape memory alloy structure 10 entirely through the inlet opening 74 and the outlet opening 78 of the folding fixture 70 and loads the structure 10 into the delivery device (not shown) such as a suitably sized delivery catheter.

The construction of the structure 10 described above allows the structure to collapse as it advances through the fixture 70. The openings 74 and 78 and intervening surface 76 can be configured to match the peripheral shape of the structure 10. The folding fixture 10 of FIGS. 9a and b is merely illustrative of the concept and FIGS. 10A-D are partial section views of a further folding fixture 10 for collapsing the lightweight, collapsible, shape memory alloy structure 10 according to the present invention. In these figures a second folding fixture with a body member 82 is provided. Body 82 is analogous to body 72 in that it contains an inlet opening 84 of a first diameter at one end thereof, a smaller diameter outlet 88 at an opposite end thereof and a converging surface 86 extending between the inlet opening 84 and the outlet opening 88. The second folding fixture is configured to have body 82 be received within the first folding fixture body 72, namely the second folding fixture body 82 is received within the outlet opening 78 of the first folding fixture body 72 with the inlet 82 receiving the structure 10 from the outlet 78 of the body 72. As shown in the figures this staged fixture construction allows for the passing of the collapsible shape memory alloy structure 10 entirely through the inlet opening 74 and the outlet opening 78 of the first folding fixture body 72 and concurrent passing of the collapsible shape memory alloy structure 10 entirely through the inlet opening 84 and the outlet opening 88 of the second folding fixture body 82. This staged folding fixture allows a gradual collapsing to occur over a limited total or effective fixture length due to the nesting of the bodies 72 and 82.

Figures 11A, 11B:
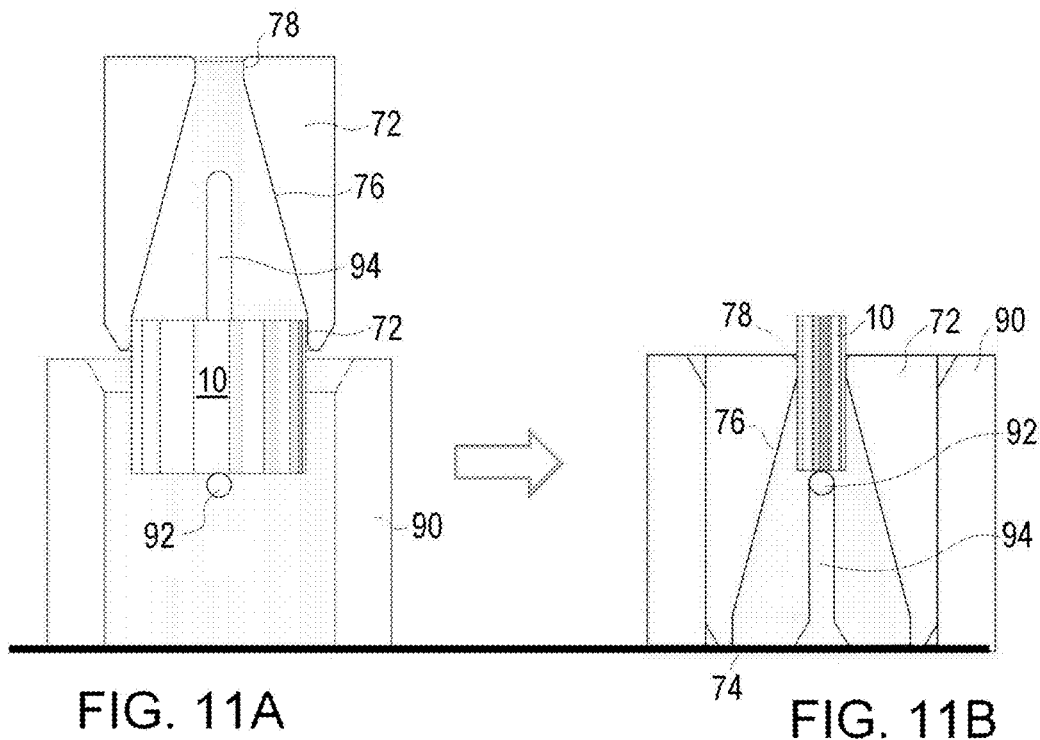
FIGS. 11A and 11B are partial section views of a further folding fixture for collapsing a lightweight, collapsible, shape memory alloy structure according to the present invention.

FIGS. 11A and 11B are partial section views of a further folding fixture for collapsing a lightweight, collapsible, shape memory alloy structure 10 according to the present invention in which a holding fixture 90 is provided for receiving and supporting the structure 10 during folding. In the illustrated embodiment a pin 92 supports the structure 10 and the folding fixture body 72 is received within the holding fixture 90 during the passing of the collapsible shape memory alloy structure 10 entirely through the inlet opening 72 and the outlet opening 78 of the folding fixture body 72. A slot 94 is in the body 72 to allow for receipt of the pin 92 during advancement of the body 72 relative to the holding fixture 90. It should be apparent that the staged folding fixture of FIGS. 10a-d could be used with a holding fixture as shown in FIGS. 11a-b.

Figure 12B:
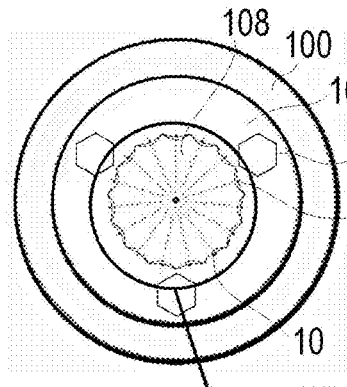
FIGS. 12A-12E are partial section views of a further folding fixture for collapsing a lightweight, collapsible, shape memory alloy structure according to the present invention.
Figure 12A:
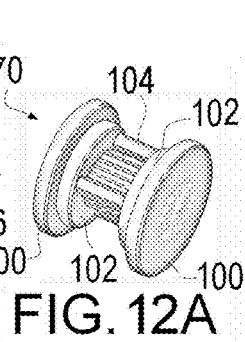
Figure 12D:
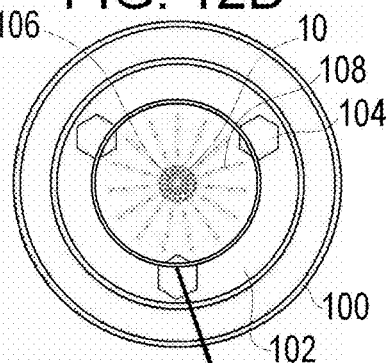
Figure 12C:
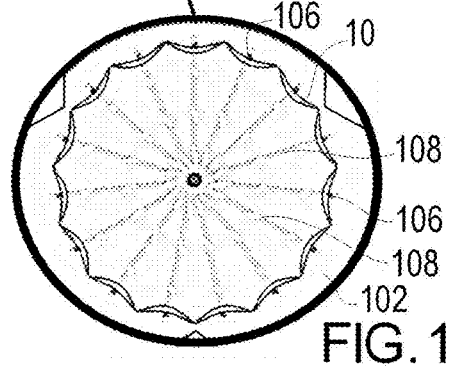
Figure 12E:
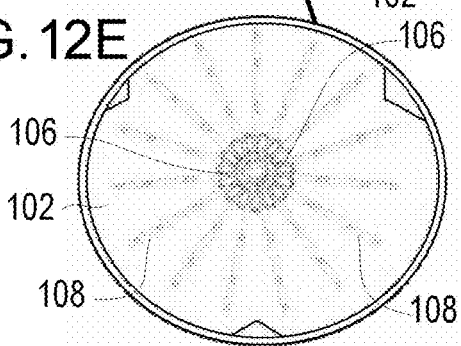

FIGS. 12A-12E are partial section views of a further folding fixture 70 for collapsing a lightweight, collapsible, shape memory alloy structure 10 according to the present invention. In this embodiment the fixture 70 includes outer control discs 102 and inner guide discs 102. The outer control discs 102 are rotatable to a certain extent relative to the inner guide discs 102. The inner discs include spacers 104 to space the one guide disc 102 from the opposed guide disc 102. A plurality of pins 106 are provided that are received and moved within grooves 108 in the opposed guide discs 102 and are also received within and moveable along helical control grooves (not shown) within control discs 100 with the associated control grooves configured to have the control discs 100 rotate opposite to each other for operation. Rotation of the control discs 100 opposite to each other will cause the pins 106 to slide along the radial slots or grooves 108. In operation one pair of discs 102 and 104 is removed to allow for insertion of the structure 10 in the position shown in FIGS. 12B and C with the pins 106 aligned with panels 32 and 22. The discs 102 and 104 are reattached to have the pins 106 engaged on both ends as shown in FIG. 12A. Rotating the discs 100 opposite to each other in one direction will cause the pins 106 to move along grooves 108 and collapse the structure 10 to the position shown in FIGS. 12D and E. The one pair of discs 102 and 104 is removed to allow for removal and loading of the collapsed structure 10 in the position shown in FIGS. 12D and E.

Figure 13A:
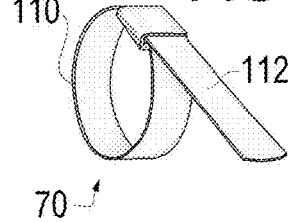
FIGS. 13A and 13B are perspective views of further folding fixtures for collapsing a lightweight, collapsible, shape memory alloy structure according to the present invention.
Figure 13B:
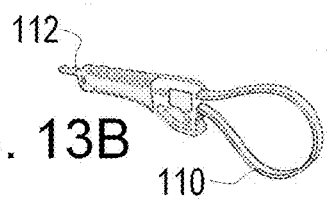

FIGS. 13A and 13B are perspective views of a further folding fixture 70 for collapsing a lightweight, collapsible, shape memory alloy structure 10 according to the present invention. In this design the folding fixture is formed of a conventional band clamping member for ease of use and operation.

The illustrated embodiments of structure 10 have shown generally circular or concentric tubular lumen shapes, however alternative geometries are possible. Conical and frustaconical structures 10 are easily designed. Further structures 10 which are non-symmetrical about a center axis may be applicable for certain implementations as would be combinations of symmetrical and asymmetrical shapes, Further, non-tubular, generally "flat panels" which are folded, for example, in an accordion fashion are possible.

Another application of the structure 10 may be as a component in an electrical circuit. Structure 10 may act as a resistor that does not change in length even with heating.

The preferred embodiments described above are illustrative of the present invention and not restrictive hereof. It will be obvious that various changes may be made to the present invention without departing from the spirit and scope of the invention. The precise scope of the present invention is defined by the appended claims and equivalents thereto.

What is claimed is:

1. A shape memory alloy implantable prosthetic structure comprising a plurality of tubular members formed of shape memory alloy material, wherein the shape memory alloy material is a nitinol material, each tubular member including a plurality of panels with each panel having side edges coupled to adjacent panels, wherein each tubular member is moveable between a radially contracted position and a radially extended position, and wherein the coupled side edges of adjacent panels of each tubular member form hinges for moving the structure between the contracted position and the extended position, and wherein the panels forming each tubular member are concave members, wherein each tubular member forms a layer of the structure and wherein the adjacent panels of adjacent layers form channels between the layers, wherein the structure forms a medical implantable prosthetic.

2. The shape memory alloy structure according to claim 1 wherein the effective outer diameter of the structure in the radially extended position is at least twice the effective outer diameter of the structure in the radially contracted position.

3. A shape memory alloy implantable prosthetic structure comprising a plurality of tubular members formed of shape memory alloy, each tubular member formed of a plurality of concave panels wherein circumferentially adjacent panels are coupled at substantial tangential portions of each circumferentially adjacent panels, and wherein each tubular member is formed for movement of the shape memory alloy structure between a contracted position and a radially extended position, wherein the structure forms a medical implantable prosthetic.

4. The shape memory alloy structure according to claim 3 wherein the adjacent panels of adjacent layers form channels between the layers.

5. The shape memory alloy structure according to claim 4 further including at least one medicament within at least one of the channels.

6. The shape memory alloy structure according to claim 3 wherein at least an outer facing surface of an outermost of the layers has distinct surface finish from an inner facing surface of an innermost of the layers.

7. The shape memory alloy structure according to claim 3 wherein one of the outer facing surface of the outermost of the layers and the inner facing surface of the innermost of the layers is substantially uniformly perforated and the other is substantially solid.

8. The shape memory alloy structure according to claim 3 wherein the structure is moveable between a radially contracted position and a radially extended position, wherein the effective outer diameter of the structure in the radially extended position is at least twice the effective outer diameter of the structure in the radially contracted position.

9. The shape memory alloy structure according to claim 3 wherein the effective outer diameter of the structure in the radially extended position is at least 3.8 times the effective outer diameter of the structure in the radially contracted position.

10. The shape memory alloy structure according to claim 3 wherein the shape memory alloy is a nitinol structure and wherein the effective outer diameter of the structure in the radially contracted position is less than about 6 mm.

11. The shape memory alloy structure according to claim 10 wherein the structure is a prosthetic cardiovascular stent.

12. The shape memory alloy structure according to claim 3 wherein the panels forming at least one tubular member are substantially solid concave members.

13. A shape memory alloy implantable prosthetic structure comprising at least two substantially concentric tubular members formed of shape memory alloy, each tubular member formed of a plurality of scalloped panels separated by peaks, and wherein at least some of the peaks of at least one concentrically inner of the tubular members are aligned with adjacent peaks of the immediately outwardly adjacent tubular member, wherein the structure forms a medical implantable prosthetic.

14. The shape memory alloy structure according to claim 13 wherein the structure is moveable between a radially contracted position and a radially extended position, wherein the effective outer diameter of the structure in the radially extended position is at least 3.8 times the effective outer diameter of the structure in the radially contracted position.

15. The shape memory alloy structure according to claim 13 wherein the shape memory alloy is a nitinol structure and wherein the effective outer diameter of the structure in the radially contracted position is less than about 6 mm.

16. The shape memory alloy structure according to claim 13 wherein the structure is a prosthetic cardiovascular stent.

17. The shape memory alloy structure according to claim 13 wherein the scalloped panels forming at least one of the tubular members are substantially solid.

* * * * *